United States Patent [19]

Kindt et al.

[11] Patent Number: 5,529,765

[45] Date of Patent: * Jun. 25, 1996

[54] RABBIT MODEL FOR DIAGNOSING AND TESTING VACCINES OR THERAPEUTIC AGENTS AGAINST AIDS

[75] Inventors: Thomas J. Kindt; Henrietta Kulaga, both of Bethesda, Md.; Thomas M. Folks, Lithonia, Ga.

[73] Assignee: The United States of America as represented by the Department of Health and Human Services, Washington, D.C.

[ * ] Notice: The portion of the term of this patent subsequent to Feb. 2, 2010, has been disclaimed.

[21] Appl. No.: 987,493

[22] Filed: Dec. 7, 1992

Related U.S. Application Data

[63] Continuation of Ser. No. 323,778, Mar. 15, 1989, Pat. No. 5,183,949, which is a continuation-in-part of Ser. No. 247,931, Sep. 22, 1988, abandoned.

[51] Int. Cl.⁶ ............................ A61K 49/00; A61K 35/00
[52] U.S. Cl. ...................... 424/9.2; 424/93.1; 424/93.21; 424/93.7; 424/93.71; 800/2; 800/DIG. 5
[58] Field of Search .................. 800/2, DIG. 5; 424/9, 89, 93 A, 93 B, 93 U, 93 T, 93.1, 93.2, 93.21, 93.7, 93.71

[56] References Cited

U.S. PATENT DOCUMENTS 5,183,949  2/1993  Kindt et al. .................... 800/2

OTHER PUBLICATIONS

Kulaga et al. (a), Proc. Natl. Acad. Sci. 85:4455–4459 (1988).
Kulaga et al. (b), J. Lenkocyte biol. 40:169–181(1986).
Kotani et al., Int. J. Cancer 37:843–847 (1986).
Alter et al., Science 226:549–552 (1984).
Marrow et al., J. Gen. Virol. 68:2253–2257 (1987).
Field, In "Antiviral Agents: the Development & Assessment of Antivirial Chemotherapy", vol. 1, pp. 67–84, 1988, ed. H. J. Field, CRC Press, Inc.

Primary Examiner—Jasemine C. Chambers
Attorney, Agent, or Firm—Townsend and Townsend Khourie and Crew

[57] ABSTRACT

A rabbit model for testing anti-AIDS therapeutic agents, vaccines, and HIV-1 infection is described.

6 Claims, 10 Drawing Sheets

Fig. 2

In vivo Infection of Rabbits with HTLV-1 and HIV-1

| Experimental Group | A301 Cells | HTLV-1* | HIV-1** |
|---|---|---|---|
| 1 | + | - | - |
| 2 | - | - | + |
| 3 | - | + | - |
| 4 # | - | + | + |

*Rabbits injected with 10*6 irradiated Mt-2 cells

**Rabbits injected IV with 5x10*6 HIV infected A301 cells

Rabbits injected with HIV infected cells after seroconversion to HTLV-1

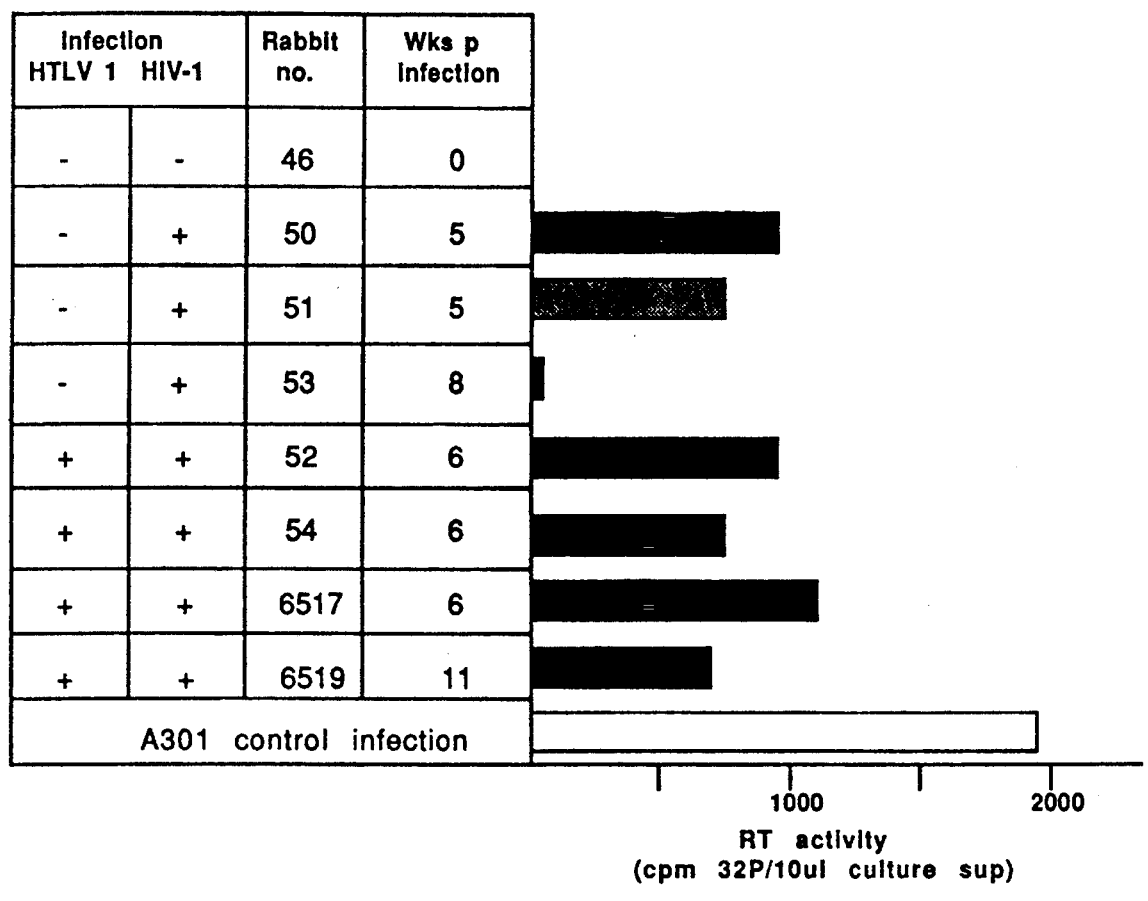
Detection of HIV in PBL of Infected Rabbits

Detection of HIV-1 DNA in Peripheral Blood Lymphocytes of Infected Rabbits

Detection of HIV-1 by the Polymerase Chain Reaction Using Primers from the gag Gene

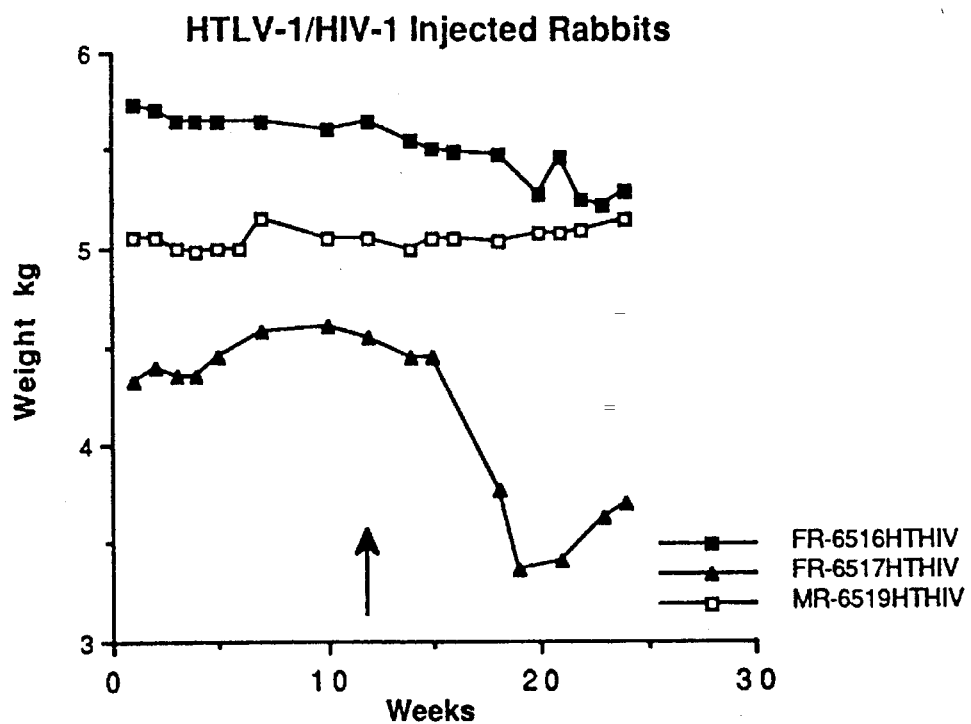
Fig. 6B
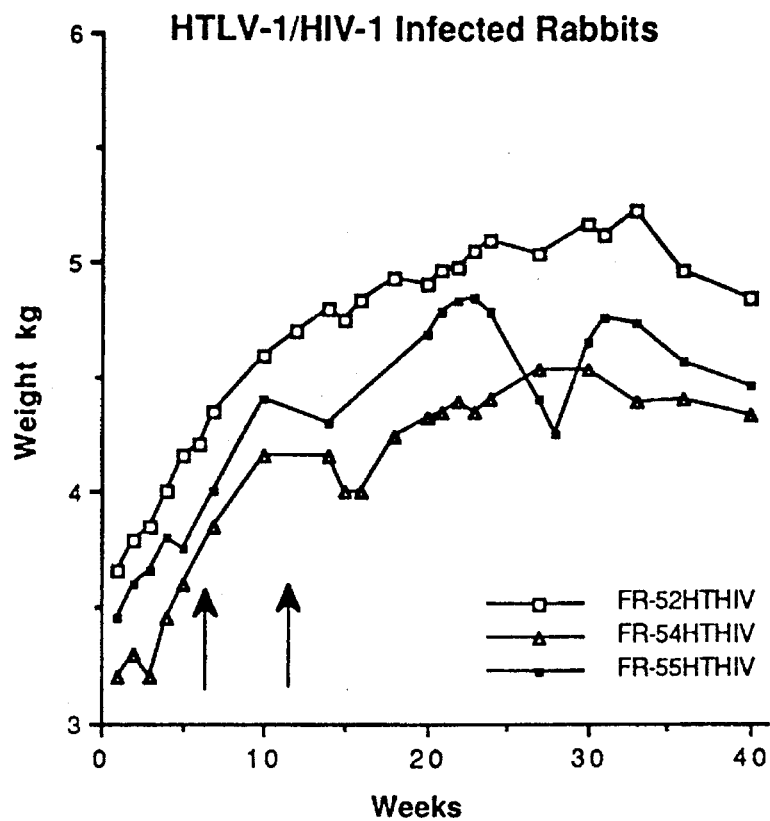

RABBIT MODEL FOR DIAGNOSING AND TESTING VACCINES OR THERAPEUTIC AGENTS AGAINST AIDS

This is a continuation of pending application Ser. No. 07/323,778, filed Mar. 15, 1989, now U.S. Pat. No. 5,183,949 which is a continuation-in-part of application Ser. No. 07/247,931 filed Sep. 22, 1988 and now abandoned, the disclosures of which are incorporated herein by reference.

TECHNICAL FIELD

The present invention is generally related to developing animal models for AIDS. More particularly, the present invention is related to providing in vitro and in vivo a rabbit model for testing infection with HIV-1.

BACKGROUND OF THE INVENTION

Numerous animal models for the acquired immunodeficiency syndrome (AIDS) disease have been attempted. A recent review by Desrosiers, et al, 1987, *Review of Infectious Diseases,* 9:438, summarizes the animal models of retrovirus infection and their relationship to AIDS. Most of these models, however, employ retroviruses other than human immunodeficiency virus (HIV-1) to produce symptoms similar to the AIDS disease in man. The chimpanzee has been infected with HIV-1, but this is an endangered species and few animals are available for research purposes. Clearly, a system that employs the human pathogen for the study and testing of the therapeutic agents, vaccines and the progressive course of the disease is preferable and is much needed for combating the deadly AIDS disease.

SUMMARY OF THE INVENTION

It is, therefore, an object of the present invention to provide an in vivo rabbit model for testing HIV-1 infection and the efficacy of vaccines and therapeutic agents against the disease caused by HIV-1.

A particular object of the present invention is to provide rabbit T-cell and macrophage lines infectible with HIV-1.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 2 is a diagrammatic representation of the experimental procedure followed for infection of rabbits with HIV-1. All animals were given a single intravenous injection of $5 \times 10^6$ cells in sterile saline solution. Group 1 animals received only A301 cells that were not infected with virus and this group served as control for the infected rabbits. Group 2 received A301 cells infected with HIV-1 and group 3 received irradiated MT-2 cells that are infected with HTLV-1. Group 4 received MT-2 cells and after seroconversion received the HIV-1 infected A301 cells.

FIGS. 6A–6D shows the weights in kilograms of rabbits before and after injection with HIV-1 and HTLV-1. Arrows show time of infection of the graphs; where two arrows are shown the first denotes the infection with HTLV-1 and the second HIV-1.

DETAILED DESCRIPTION OF THE INVENTION

Figure 1:
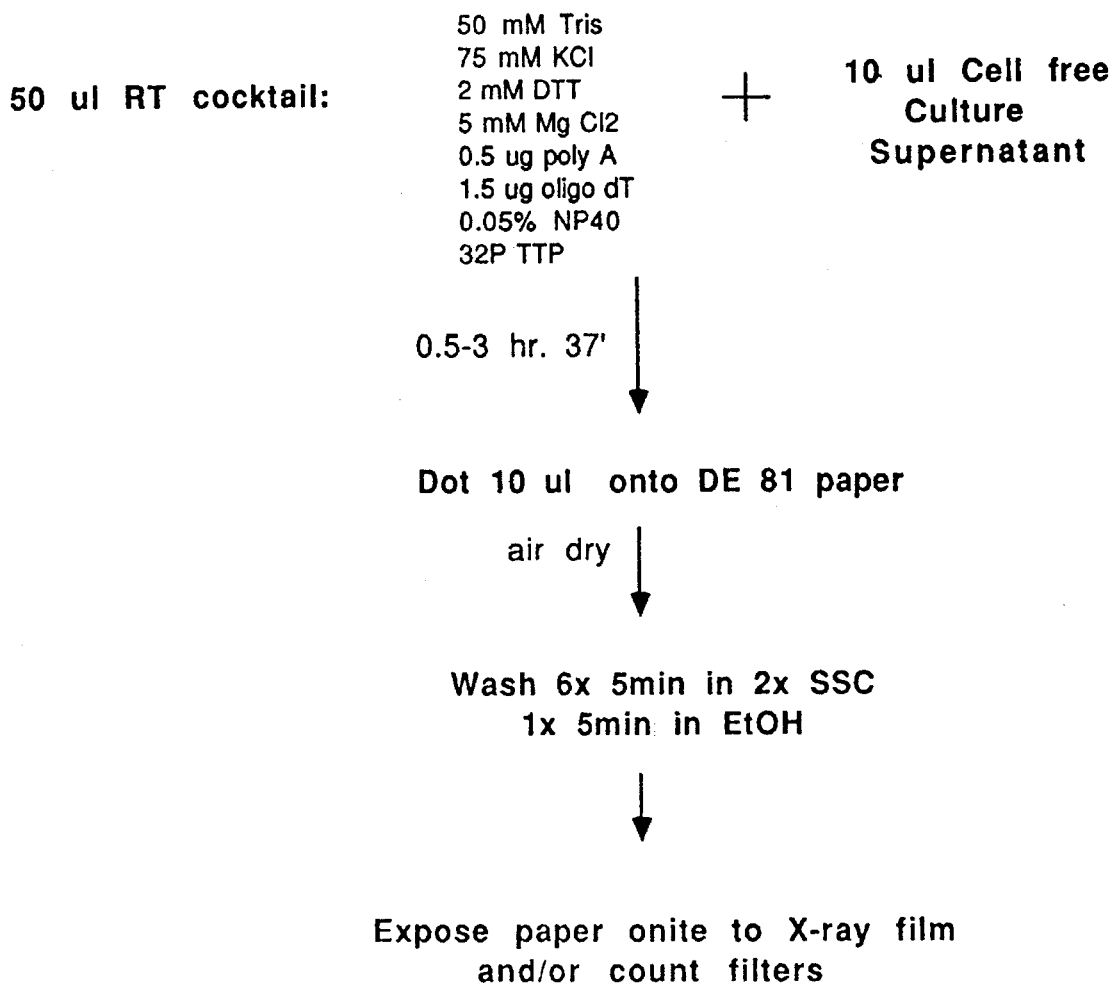
FIG. 1 is an outline of the assay used to measure reverse transcriptase (RNA-directed DNA polymerase, EC 2.7.7.49) activity in cell free supernatants from cultures potentially infected with HIV. This procedure is a modification of the assay of Goff et al. J. Virol. 38 239 (1981) as described by Willey et al. J. Virol. 62 129 (1988).
Figure 3A:
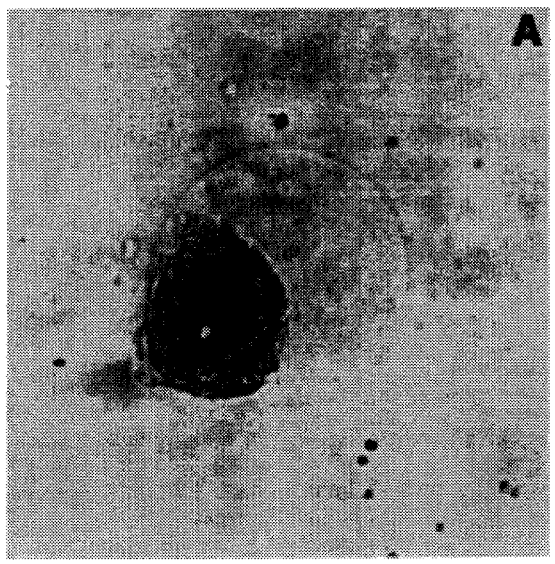
FIG. 3 shows photomicrographs of syncytia formation in IL-2 supplemented cultures of rabbit peripheral blood cells (PBL) taken from singly (3A, 3B) or doubly (3C) infected animals. PBL from a doubly infected rabbit were cultured in the presence of A301 cells are shown in FIG. 3D. Supernatants were taken at regular intervals and tested for the presence of RT. Values are shown for 10 ul of culture supernatant (FIG. 3E).
Figure 3B:
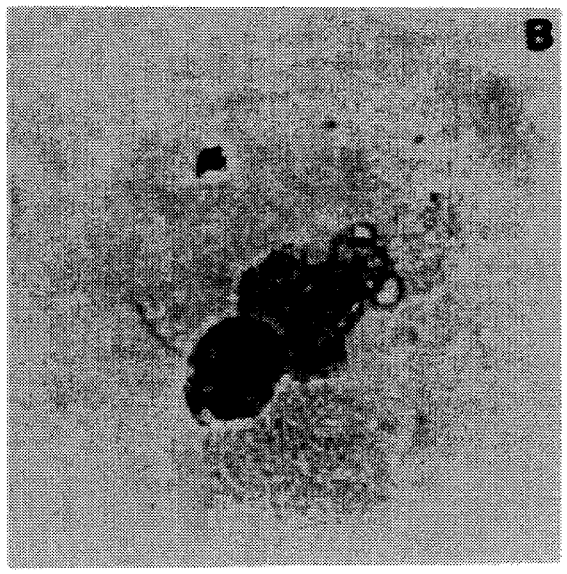
Figure 3C:
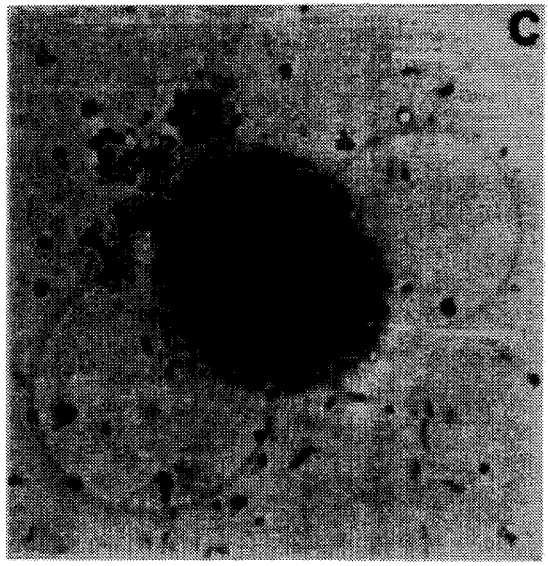
Figure 3D:
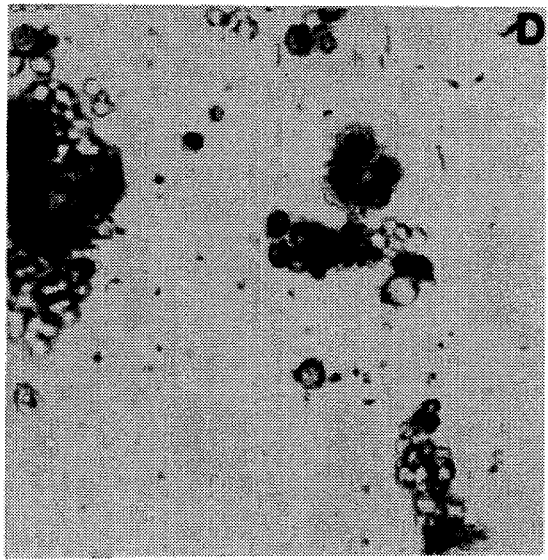

The above and various other objects and advantages of the present invention are achieved by an animal model for testing vaccines and therapeutic agents against AIDS, comprising live rabbits methodically infected either with HIV-1 alone or coinfected with HTLV-1; and rabbit T-cell and macrophage lines infectible with HIV-1.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

IN VIVO MODEL

The materials and methods for in vivo system are now described.

As a first step, the rabbits (*Oryctolagus cuniculus*) are injected with human T-cells infected in vitro with HIV-1 and subsequent observation of the rabbits for: antibodies against the proteins of HIV-1, the presence of virus in peripheral blood cells and signs of disease that are similar to those observed in human individuals infected with HIV-1. The rabbits to be infected should have had no previous history of experimental viral infection or, alternatively, may have been infected with the virus HTLV-1 prior to infection with HIV-1.

Selection and preparation of rabbits

Outbred rabbits are used for the tests. New Zealand White rabbits are preferred. Young rabbits (6 months to 1 year old) are obtained and housed according to acceptable standards for laboratory rabbits. The animals are ascertained to be healthy and to have no antibodies reactive with HIV-1 proteins as determined by standard ELISA prior to onset of experimental infection with HIV-1. Prior to infection whole blood and serum samples are taken for routine clinical testing including hematology and serum chemistry. Rabbits for which tests fall within normal ranges are chosen. Weights of the rabbits are determined about every two weeks and observation of gross state of health is frequently made. Measured amounts of food are given so that intake may be monitored. Rabbits that experience weight loss, have diarrhea, external lesions or any other evidence of poor health are rejected. Serum samples are retained at −20° C. for all rabbits to be subsequently infected with HIV-1.

Following another strategy, rabbits previously infected with HTLV-1 are used; these are shown by serologic testing to have antibodies directed against this virus but otherwise their clinical status is monitored in the same way as the others. Additional possible variations include the use of rabbits into which foreign genes (transgenes) encoding different molecules that may enhance infection with HIV-1 have been introduced.

Infection of rabbits with HTLV-1

Rabbits are given an intravenous injection with the cell line MT-2 ($5 \times 10^6$) cells. Prior to injection the cells are irradiated at 10,000 rads to promote virus shedding. Serum samples are taken at 2 week intervals and tested by a commercially available kit (Dupont) for the presence of antibodies directed against HTLV-1 proteins.

Infection of rabbits with HIV-1

Rabbits are given a single intravenous injection with $5 \times 10^6$ human cells that have been infected with HIV-1 and that are at the peak of infection as indicated by reverse transcriptase (RT) activity in the cell culture supernatants and by the presence of syncytia. Syncytia formation is monitored microscopically and scored by reference to cultures of the same line that have not been infected with the virus as well as other productively infected cultures. Reverse transcriptase activity is monitored by an assay that measures formation of insoluble radioactive nucleic acid polymers from a mixture containing the test sample and $^{32}P$ dTTP, poly A, oligo dT primers in the presence of ions and buffers necessary for the enzymatic activity of HIV-1-RT (FIG. 1). The infected cells are pelleted by centrifugation and $5 \times 10^6$ cells taken into a volume of 1 to 2 ml of sterile saline in a syringe fitted with a 23 gauge needle. The human cell line used here is A301, a T-cell leukemia derived line.

For the safety of workers and to minimize stress on the part of the animals the rabbits are sedated prior to injection with the HIV-1 infected cells using a 1:1 vol:vol mixture of zylazine 20 mg/ml (Rompun, Mobay Corp., Shanee, Kan.) and ketamine.HCl 100 mg/ml (Bristol Labs, Syracuse, N.Y.) given by intramuscular injection. The amount used is based on the body weight of the rabbit; 0.3 ml per kg is typically used. When this dose fails to induce proper sedation (about 10% of rabbits in our experience) an additional injection ½ the volume of the first drug dose is given. The sedated animal is restrained, the ear is shaved and the HIV-1 infected cells are injected into the marginal ear vein. Care is taken to remove any blood from the ear after withdrawal of the needle; this is done with 70% alcohol. Any spills are immediately wiped clean with alcohol or with a 10% solution of household bleach. All injection materials are placed in container containing undiluted household bleach for at least 10 minutes prior to disposal in hard plastic containers intended for this purpose. Needles are never recapped.

Animals are housed in a facility to which access is strictly limited to investigators and personnel in charge of the animal care. Those entering the room must wear disposable lab gowns or coveralls, face masks and shoe covers; eye protection is worn for bleeding or any procedure that may result in splashing of blood or other body fluid. Rabbits taken out of their cages for weighing, bleeding or other procedures are never left unattended and are transported to treatment rooms in a restraining box on a laboratory cart. All waste products are disposed of as Medical pathological waste. Necropsy procedures are carried out in a biological safety cabinet.

Monitoring of rabbits following HIV-1 infection

Rabbits are monitored for weight loss and for any signs of illness including the presence of external lesions, any abnormal swelling, secretions from eye, ear, nose, or mouth, diarrhea, changes in food or water consumption as well as for signs of lethargy and for neglect of self grooming. Blood samples are periodically taken and whole blood and serum is submitted for hematologic and chemical profiles.

Peripheral blood samples are taken under sterile conditions and lymphocytes isolated and placed in culture with interleukin-2 or in the presence of a human T-cell line that is highly susceptible to infection with HIV-1. Cultures are monitored for the formation of syncytia and cell free supernatants are taken from the cultures and RT activity is measured. Supernatants are used to infect large cultures of human cells and the DNA is isolated from these cells after infection is evident. This DNA is analyzed for the presence of HIV-1 sequences by Southern blot analysis using probes specific for the HIV-1 genome. The DNA samples are also analyzed using the polymerase chain reaction technique with primers selected from the relatively well conserved portions of the HIV-1 genome. The amplified sequences are detected by visualization of fragments of the appropriate size after electrophoresis on agarose gels. The fragments are then digested using restriction endonucleases and sizes of the fragments obtained are compared with sizes expected from observation of the reported map of the HIV-1 genome.

Southern blot analysis of the fragments using probes derived from the regions of the gene that have been amplified may be used to verify that the amplified fragment derives from the appropriate region of the HIV-1 genome; it may also be used as a more sensitive detection method if no fragments are visualized with ethidium bromide in the initial screening.

Certain animals are sacrificed by lethal injection of anesthetic and organs (usually liver, lungs, kidney, appendix, heart and brain) are fixed in formalin and submitted to a registered veterinary laboratory for diagnostic pathology. Spleens from infected animals are weighed and divided into sections for pathology, for cell culture and a final portion is frozen for future analyses.

RESULTS

In initial experiments a group of six rabbits that have been seroconverted to HTLV-1 and three rabbits with no previous treatment were injected with A301 cells that were HIV-1 infected. Two rabbits were given A301 cells that were not infected and five rabbits that were infected only with HTLV-1 were used as controls for the tests (FIG. 2). Bleedings taken from these rabbits at three week intervals following infection were tested by a Dupont ELISA kit for the presence of antibodies against HIV-1 proteins. Serum samples from an AIDS patient were used as positive control and the rabbit samples were scored as percent of the OD value given by the positive control. All values were calculated after the subtraction of background OD values; preinfection serum from the infected rabbits was used as negative control to ascertain the background. Samples giving 30% of positive control values were considered positive. The samples that were positive for an ELISA were then tested by Western blot analysis using strips of nitrocellulose that contain separated HIV-1 proteins (Epitope Inc.) and developed with gold labeled goat-anti-rabbit antibodies (Janssen). Results of these tests are given in Table 1. All rabbits that were injected with infected A301 cells and none that were injected with the uninfected controls were positive by ELISA; the bleedings tested by Western blot analysis were also positive for antibodies against certain of the HIV-1 proteins.

Peripheral blood lymphocytes (PBL) were taken from the experimental animals and cultured at a density of $5\times10^5$ cells/ml with units/ml interleukin 2 in RPMI 1640 medium containing 10% fetal bovine serum. Duplicate cultures lacking interleukin 2 were cultured in the presence of A301 cells added at a density of $1\times10^5$ cells/ml. All cultures were observed for the formation of syncytia and supernatants taken for RT testing (FIG. 3). Syncytia were seen in cultures from infected animals 5 weeks after infection and approximately two weeks in culture (FIGS. 3A–D). Supernatants from cultures with evident syncytia tested positive for RT activity in most cases. These positive supernatants were saved and used to infect large scale cultures of A301 cells.

Figure 4:
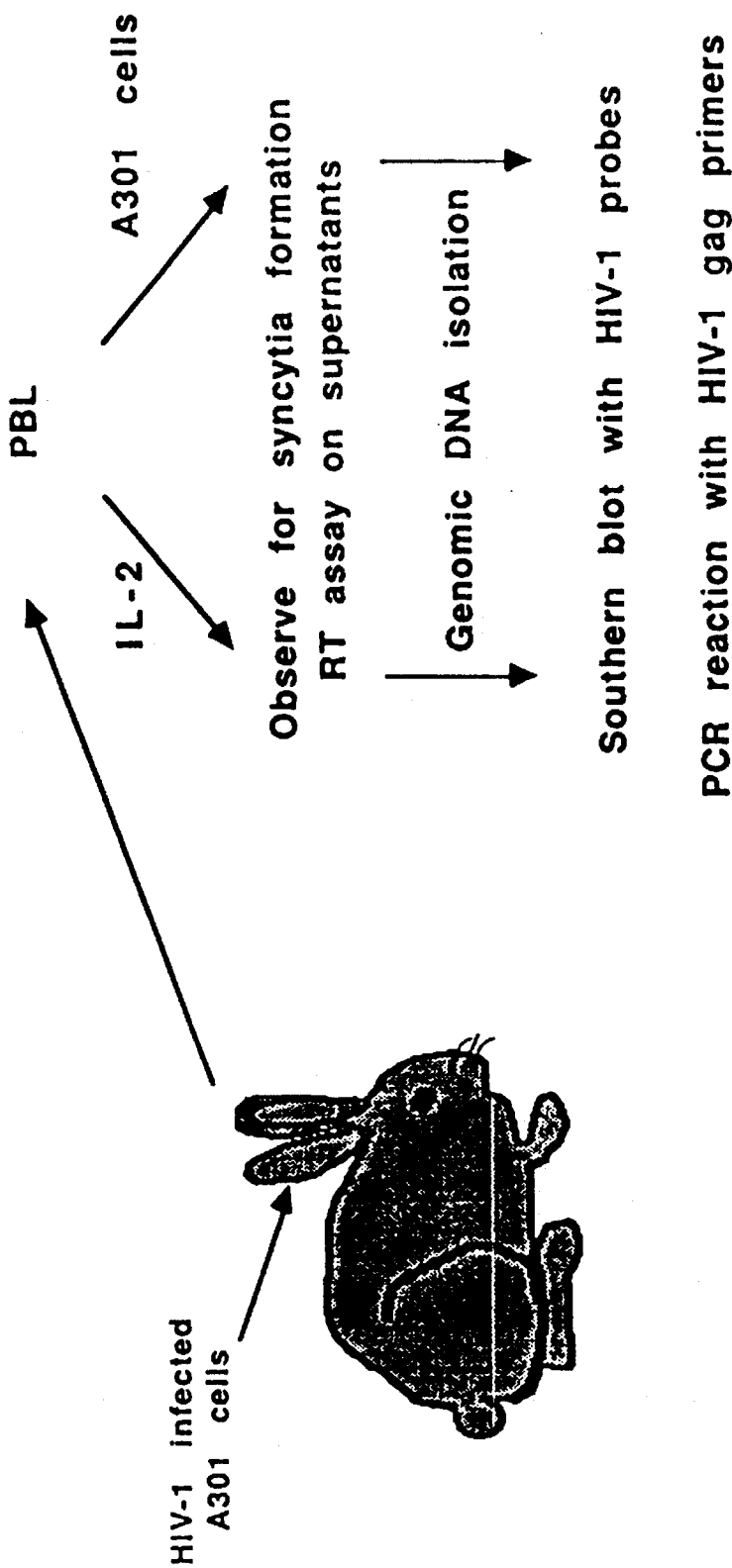
FIG. 4 shows the procedure for expansion of virus obtained from PBL of infected rabbits in order to obtain amounts sufficient for analysis of DNA.

Further evidence that the rabbit cells were HIV-1 infected and not infected with other retroviruses of rabbit origin come from studies of DNA from the A301 cells that were infected with the supernatants from the rabbit cells that were cultures in IL2 or cocultured with A301 cells (FIG. 4). DNA was isolated from these cells by standard procedures and digested with the restriction endonuclease Hind111. Southern blot analysis of this DNA using probes derived from the proviral genome of HIV-1 confirmed the presence of HIV-1 DNA.

Figure 5A:
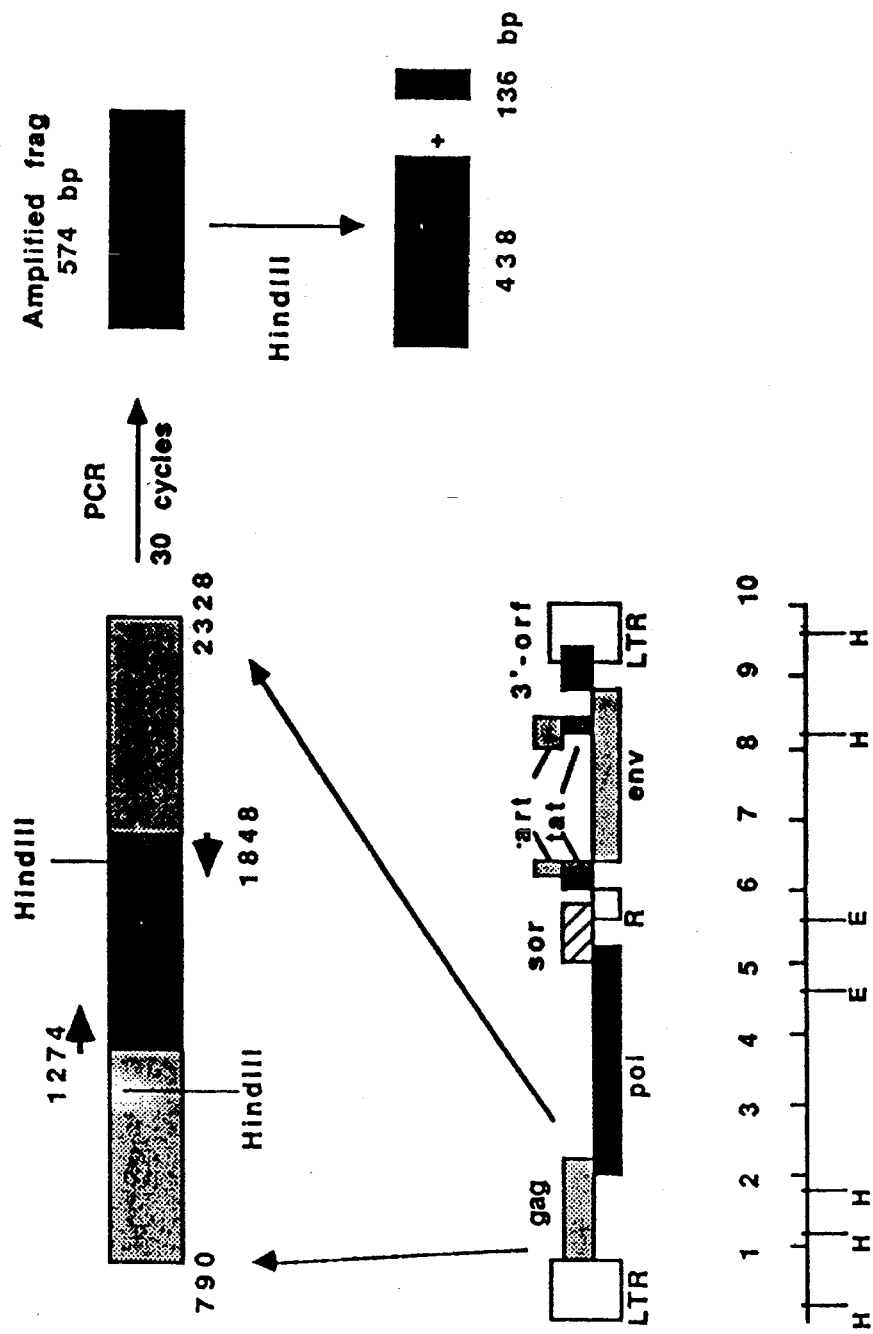
FIG. 5A is a schematic representation of the polymerase chain reaction to detect HIV-1 DNA in the DNA samples extracted from cultures of infected cells. The diagram shows on the bottom left a representation of the HIV-1 genome and an expanded drawing of the gag gene with region to be amplified shown in black. The numbers shown below the diagram of the gag gene are for the LAV isolate of HIV-1. The primers used are 20 bases in length and were selected for conservation in various isolates of HIV-1.
Figure 5B:
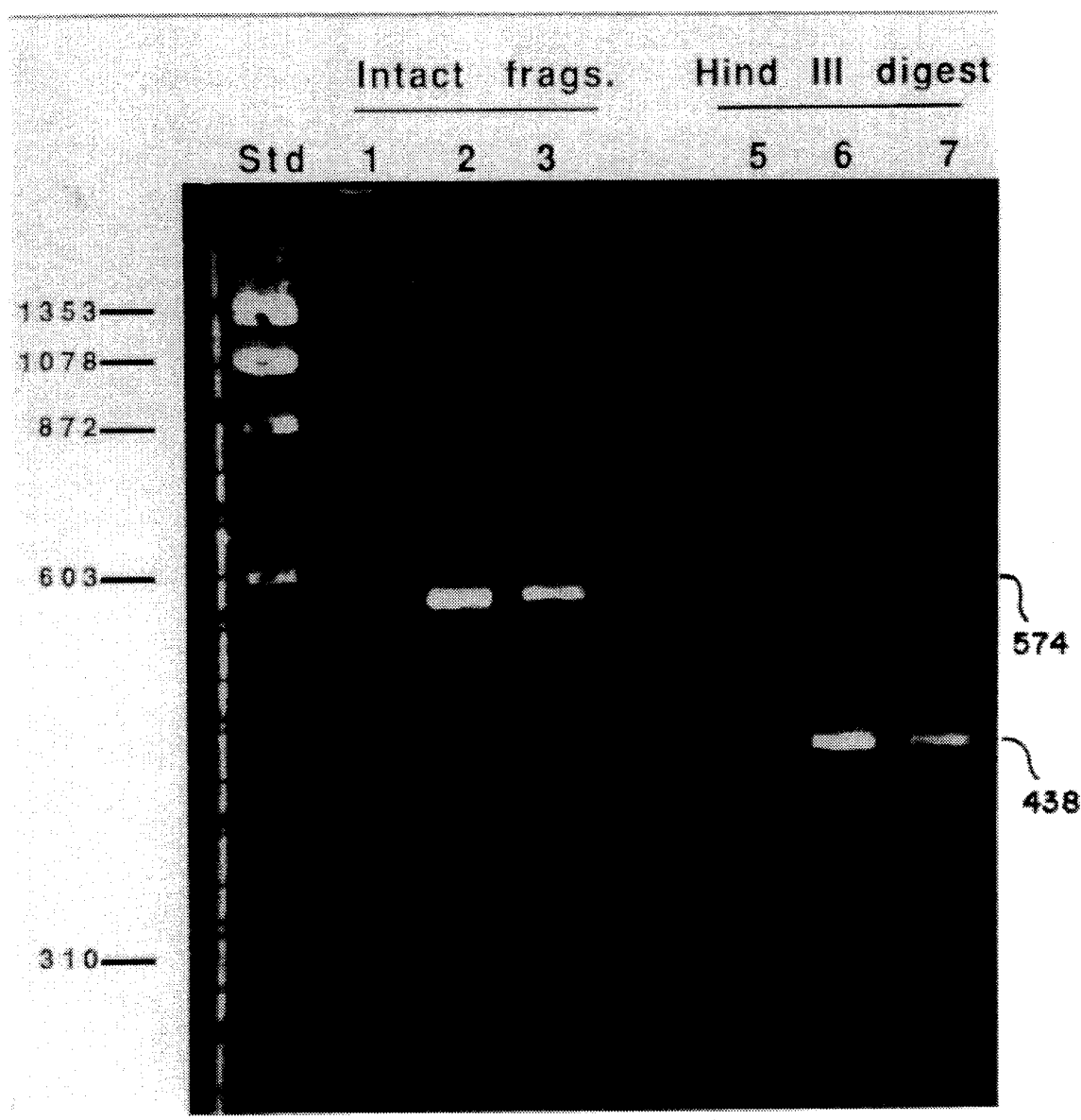
FIG. 5B shows the results obtained from a portion (~10%) of the final reaction mixture electrophoresed on an agarose gel with standards (HaeIII digested x174 DNA fragments) for size determination before (lanes 1, 2 and 3) and after lanes 5, 6 and 7) cleavage with the restriction endonuclease HindIII and the products visualized under ultraviolet light after reaction with ethidium bromide.

The DNA samples were further subjected to analysis using the polymerase chain reaction technique with synthetic oligonucleotide primers with sequences based on the reported sequence of the isolate of HIV-1 (LAV) used in these studies. The primers were from the gag region of the gene and the inclusive sequence spanned a stretch of 574 bp. The validity of the fragment obtained by 30 cycles of amplification was shown not only by its conformity to the expected size, but also by the presence of restriction enzyme sites in the positions expected from the published sequence (FIG. 5). The fragment obtained and the digest fragments were visualized not only by ethidium bromide staining, but also by Southern blot analysis of the gels that were used to separate the products of the PCR reaction. These blotting studies used probes from the HIV-1 genome.

Figure 6C:
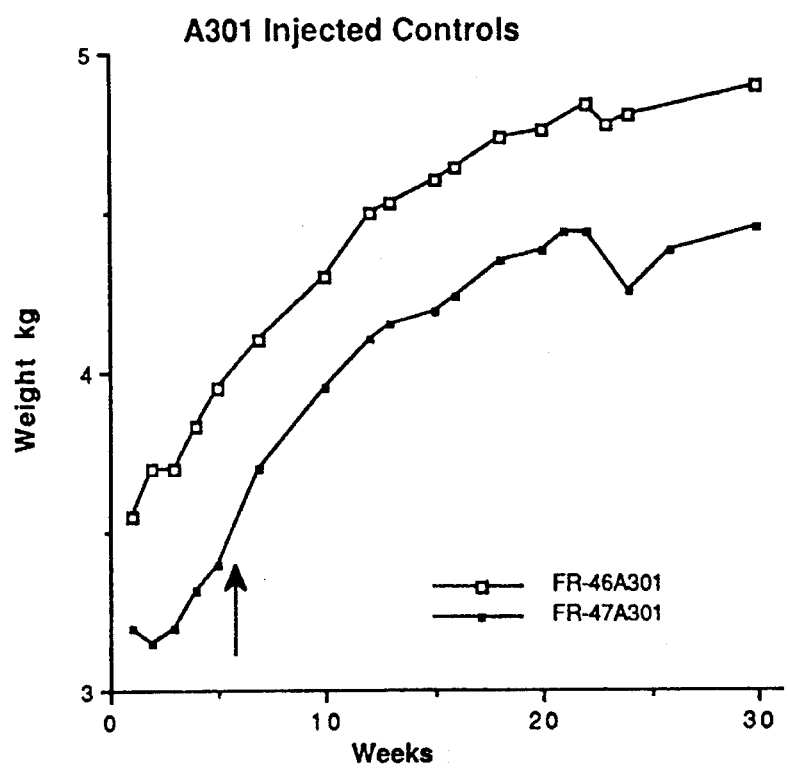
Figure 6D:
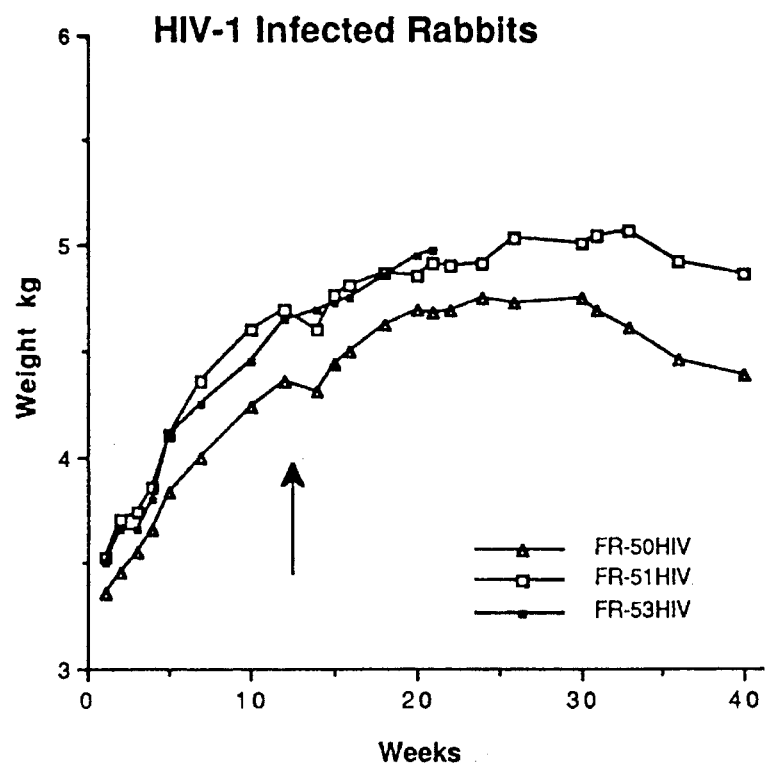

The results indicated that the rabbits were infected with HIV-1 and further showed that the virus had not significantly mutated in the rabbit. The rabbits were also monitored closely for sign of clinical illness (Table 2). Evidence for illness caused by the HIV-1 infection appeared to be more profound in those animals that were infected with both HTLV-1 and HIV-1. Significant weight loss was observed in two of the doubly infected animals and a gradual decline in weight in others (FIG. 6A); all animals in this group had diarrhea at one time or another following infection with HIV-1. Clinical testing showed no evidence for anemia and no gross changes in serum chemistry were observed. Ratios of lymphocytes to polymorphs in certain of the animals drastically changed with large variations in the lymphocyte count and modest decreases in the total WBC. Overt signals of illness were not seen in the animals infected with HIV-1 alone.

Necropsy was carried out on two rabbits that were injected only with HIV-1 at 2 months and at 7 months after infection. Spleen, kidney, lungs and liver were taken from the first and all these along with brain, heart and appendix from the second. Several of the doubly infected animals and control animals either injected with A301 cells or with HTLV-1 alone were also sacrificed and organs taken at necropsy for pathology. An excerpt from the pathology reports is presented in Table 3. Spleen cells from rabbit 53 (2 months post infection) were analyzed by flow cytometry using monoclonal antibodies directed against human cell surface markers (Becton Dickinson, Mountain View, Calif.).

TABLE 1

Antibody Reactivity in HTLV-1 and HIV-1 Infected Rabbits

| Experimental Group | Animal no. | ELISA results# HTLV-1 | HIV-1 | WB analysis* |
|---|---|---|---|---|
| HTLV-1 only | 48 | 76 | 2 | — |
| | 49 | 82 | 4 | nd |
| | 45 | 59 | 0.6 | nd |
| | 6518 | 64 | 1 | nd |
| | 6520 | 90 | nd | nd |
| HIV-1 only | 50 | 3 | 48 | 160, 120 |
| | 51 | 3 | 43 | 160, 120, 51, 18 |
| | 53 | 1 | 64 | 160, 120, 51 |
| HTLV-1/HIV-1 | 52 | 81 | 78 | 160, 51 |
| | 54 | 45 | 89 | 51 |
| | 55 | 76 | 66 | 160 |
| | 6516 | 52 | 51 | nd |
| | 6517 | 67 | 47 | nd |
| | 6519 | 49 | nd | nd |
| A301 cells | 46 | nd | 0 | — |
| | 47 | nd | 0 | nd |

ELISA numbers are given as % of positive control for bleeding with peak value

TABLE 1-continued

Antibody Reactivity in HTLV-1 and HIV-1 Infected Rabbits

| Experimental | | ELISA results# | | |
|---|---|---|---|---|
| Group | Animal no. | HTLV-1 | HIV-1 | WB analysis* |

*Western blot (WB) results are given in kd for HIV proteins visualized with rabbit sera. All bands seen are recorded although not all were present at each time point.

TABLE 2

Clinical signs of illness monitored in HTLV 1 and HIV infected rabbits

Seroconversion
General appearance self grooming
any abnormal swelling or external lesions
secretions from eye ear nose or mouth
evidence of diarrhea
Weight loss
Blood testing serum protein, electrolytes and enzymes
hematologic profile
Macroscopic and microscopic examination of organs from autopsied animals University) and 6083 is a macrophage transformed with SV40; 5943 and 6057 are adenocarcinoma lines derived from breast tumors at autopsy. UTfib is a uterine fibroma derived from a surgical specimen. Yc/c LIV is a liver fibroblast and R-2 is a splenic fibroblast; both were taken from normal rabbit tissue. All rabbit lines were maintained in RPMI 1640 with 10% fetal calf serum supplemented with glutamine (2 mM) and penicillin streptomycin. Human T-cell lines SupT1 and A3.01 were maintained in RPMI 1640 with 10% fetal calf serum. Isolation of rabbit peripheral blood lymphocytes (PBL) was on Ficoll Hypaque by standard methods (Kulaga, et al. 1986, *J. Leuko. Biol.* 40, 169–181). PBL were activated by incubation with 10 ug/ml Con A; 20 ug/ml PHA; with 500 units/ml recombination human interleukin-2 or by incubation with allogeneic lymphocytes at a 1:1 ration. PBL cultures were infected with HIV-1 three days after initiation of treatment. Cell viabilities were determined by trypan blue exclusion.

Infection. Cell pellets were incubated with high titered HIV-1 stock (LAV) in the presence of 1 ug/ml polybrene (Givco, Grand Island, N.Y.). After two hours at 37° C., cells were diluted to a density of $5\times10^6$ cells/ml. The following day cells were pelleted and washed twice in complete medium and resuspended to a density of $10^6$ cells per ml. Cultures were rested for two days before samples of cell free medium or infected cells were taken for various assays.

Reverse transcriptase assay. RT activity was determined for 10 ul samples of cell free supernatant using the assay as described herein supra. Quantitative data were obtained by counting filters in scintillation fluid.

TABLE 3

PATHOLOGY OF ORGANS FROM INFECTED RABBITS

| Rabbit | Treatment | Sac. days pHIV-1 inj. | Status at sac | HIV-1 Ab | virus | Organs | | | | |
|---|---|---|---|---|---|---|---|---|---|---|
| | | | | | | Spleen | Lung | Kidney | Liver | Other |
| 6518 | HTLV-1 | NA | OK | – | – | mild hemosiderosis | normal | normal | min lym periportal hepatitis | — |
| 6516 | HTLV-1/ HIV-1 | 80 | swelling breasts l. nodes diarrhea | +++ | ± | lymphoid hyperplasia | multifocal hemorrhage mild bronchitis and pneumonia | mild focal interstitial nephritis | active cholangio hepatitis | breast-papillary adenocarcinoma adenomatous hyperplasia |
| 6517 | HTLV-1/ HIV-1 | 75 | transient paralysis, weight loss diarrhea | ± | ± | lymphoid hyperplasia mild hemosiderosis | active bronchitis | tubular dilation interstitial nephritis | active cholangio-hepatitis | |
| 53 | HIV-1 | 60 | diarrhea | + | ± | lymphoid hyperplasia amyloid-fibrin- | normal | tubular mineralization | normal | T cell from spleen |

It is clear from the evidence presented herein that the rabbits infected with HIV-1 in accordance with the present invention do serve as a model system for the study of in vivo HIV-1 infection.

IN VITRO MODEL

Evidence is now presented for the infection of two rabbit T-cell lines and a macrophage line with HIV-1. Sequential samples of the infected cultures were tested and shown to be positive for viral protein and RNA. The susceptible lines have been shown to be of rabbit origin by studies at the nucleic acid level and by cell surface markers.

Cell lines. RL-5 is a rabbit T-cell line obtained by transformation with *herpesvirus ateles;* 446 is a T-cell line transformed with HTLV-1 (obtained from Dr. Seto, Kyoto Fluorescent Antibody Assays. For immunofluorescence assays infected and uninfected cells (approximately $3\times10^5$) were cytospun (700×g, 5 min), fixed in acetone at 4° C., washed in PBS and incubated with a 1:1000 dilution of either normal human serum or an AIDS patient serum for 30 min at room temperature (22°–25° C.), washed in PBS and then reacted with fluorescein-conjugated goat anti-human IgG for 30 min at room temperature (22°–25° C.). After washing, cells were mounted and viewed under a UV microscope.

Northern Blot Analyses. Total cellular RNA was isolated by homogenization of cells in 4.23M guanidinium isothiocyanate and pelleting through a CsCl gradient. Samples of 5

μg glyoxalated RNA were electrophoresed on a 1% agarose gel run in 0.1M sodium phosphate and blotted onto a nitrocellulose filter. Filters were dried and baked for 2 hr. at 80° C. and then prehybridized at 42° C. for 16 hrs. Probes were nick translated with $^{32P}$dCTP and added to the filter in hybridization mixture and incubated for 18 hrs. at 42° C. After several washes in 2×SSC (0.3M NaCl, 0.03M NaCitrate) at room temperature the filters were washed in 1×SSC twice at 52° C.

Western Blot Analyses. Cultures were harvested at various times after infection. After washing with culture medium, $10^8$ cells were pelleted in a microfuge tube and 100 ul lysis buffer was added with vortexing. Samples were placed on ice for 15 min., centrifuged and supernatant taken for electrophoresis. Lysis buffer was 50 mM Tris pH 8.0, 5 mM EDTA, 100 mM NaCl containing 0.5% CHAPS (Calbiochem, San Diego, Calif.) and 2% deoxycholate (Sigma Chemical Co., St. Louis, Mo.). Proteins were separated on a 3–27% gradient Tris SDS-polyacrylamide gel, transferred to nitrocellulose, and allowed to react with an AIDS patient serum. $^{125}$I-labeled protein-A was then used to detect immunoreactive proteins. Filters were dried and exposed to XAR-2 films with an intensifying screen at −70° C. A lysate obtained from an HIV-1 infected human T-cell culture (A3.01) was used as a positive control.

Figure 7A:
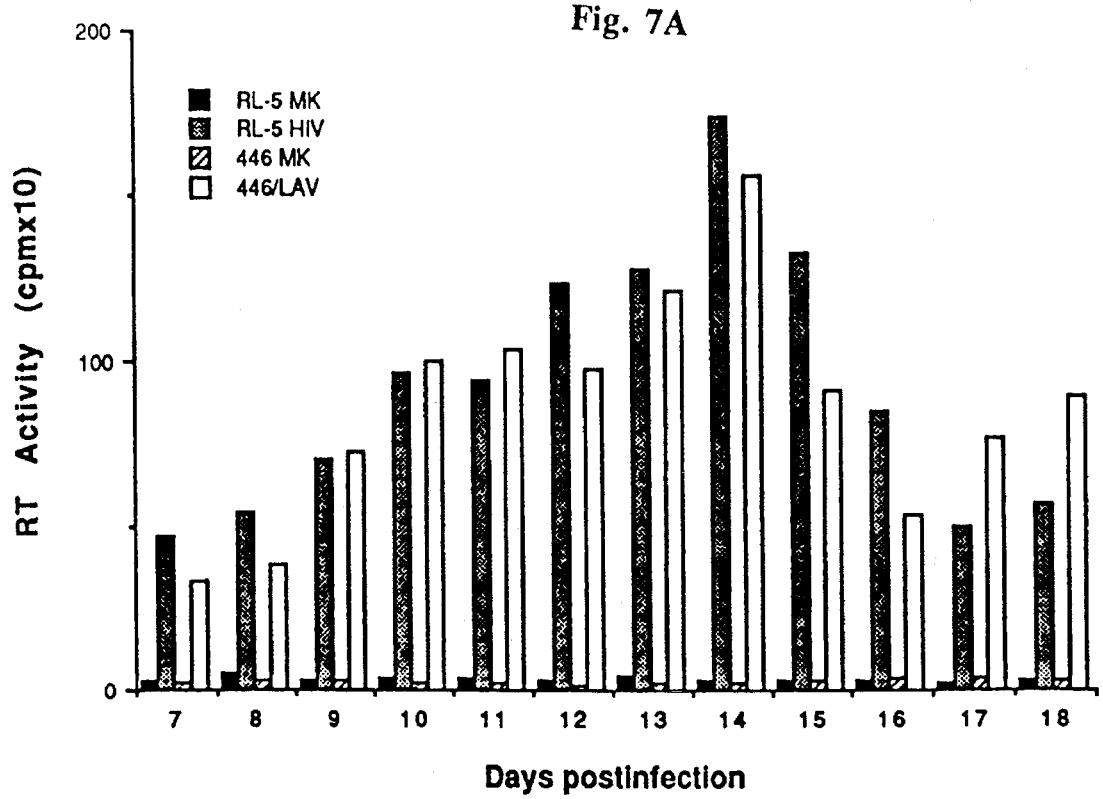
FIG. 7A shows the kinetics of RT activity in infected (HIV) and mock infected (MK) cultures of the rabbit T-cell lines RL-5 and 446. The RT data are expressed as $^{32P}$cpm/10 ul of reaction mixture.

Results from cell-free supernatants monitored daily for reverse transcriptase (RT) activity as shown in FIG. 7A show that RT activity rises in both T-cell lines 7 to 10 days post infection and peaks at approximately 14 days post-infection and then declines. The time of occurrence and magnitude of RT activity varied somewhat from infection to infection depending on the viral stock utilized, but all attempts to infect RL-5 and 446 have been successful. No RT activity was detected in mock-infected cultures of RL-5 or 446 cells.

Figure 7B:
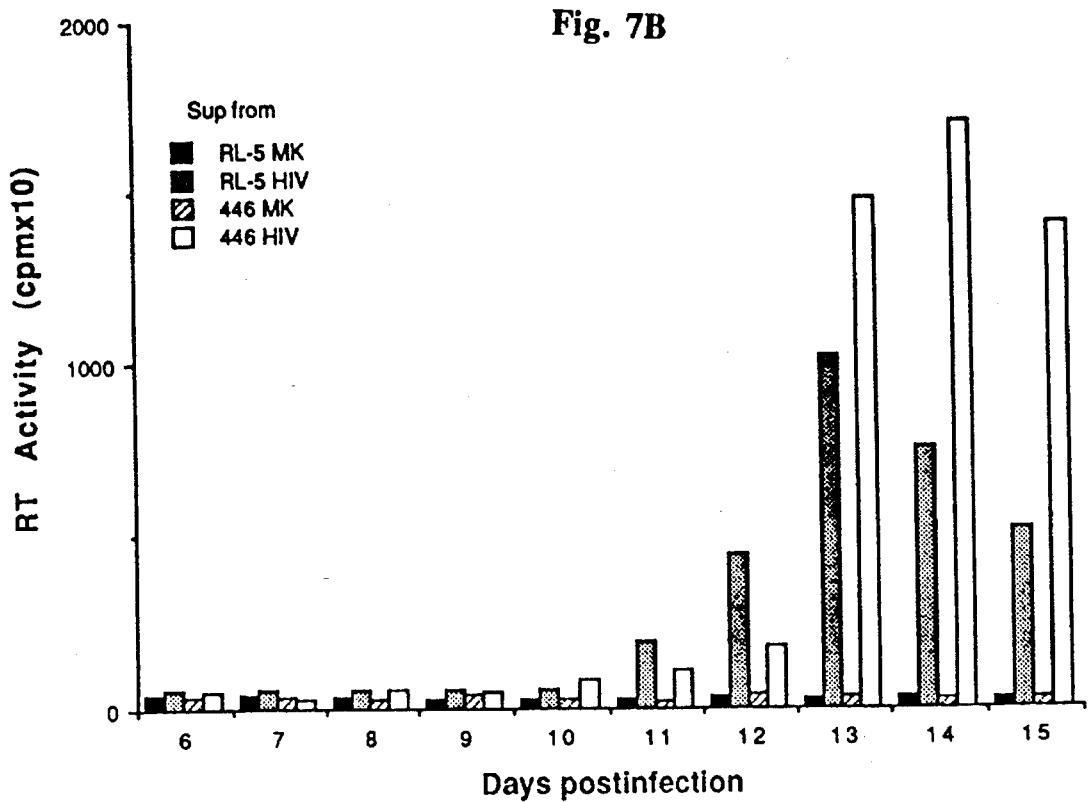
FIG. 7B shows the infectivity of cell free supernatants from rabbit cell cultures in human indicator cells. Supernatants (sup) were taken from infected (HIV) or mock infected rabbit (MK) cultures and mixed with human T-cell line SupT1. RT activity is expressed as in 1A. Syncytia were first observed in SupT1 cultures infected with supernatant from HIV infected RL-5 and 446 cells on days 11 and 10 respectively. No syncytia were observed during a 20 day observation period in SupT1 cultures given rabbits from mock infected rabbit cells.

The ability of cell free supernatants collected at the time of peak RT activity from HIV infected rabbit cells to infect a highly susceptible human T cell line, SupT1 is shown in FIG. 7B. A thousand-fold increase in RT activity can be seen in SupT1 cultures incubated with RL-5 or 446-derived supernatants along with induction of syncytia formation just prior to peak RT activity. No detectable levels of RT activity were observed in SupT1 cultures incubated with supernatants from mock-infected rabbit T-cells.

Attempts were made to infect other continuous rabbit cell lines and primary cultures of lymphoid and nonlymphoid origin. As shown in Table 4 only the RL-5 and 446 T-cell lines were susceptible to HIV infection as detected by RT activity and by passage of infectious virus in cell-free supernatants to a human indicator line. One macrophage line, 6083 was negative for RT activity, but its supernatant taken at day 11 was infectious for the human indicator line. Rabbit peripheral blood lymphocytes activated by mitogens, by growth in the presence of human recombinant interleukin 2 (Il-2) or by mixed lymphocyte culture did not support infection even though these cultures are expected to be rich in T-cells.

In subsequent large scale infections, the relationship among RT activity, cell viability and immunoreactivity with an AIDS patient serum by indirect immunofluorescence and Western blot analysis was examined. RNA was isolated from these infected cells for Northern blot analysis. Data from these infections show that for RL-5 and 446 the number of viable cells fell dramatically just before peak RT activity (Kulaga, et al, 1988, PNAS, U.S.A., 85:4455). Positive immunofluorescence was observed for cells in the HIV-infected cultures prior to peak values of RT activity; the highest percentage of antibody reactive cells (approaching 50%) occurred just prior to the time of peak RT activity. Lowest values for cell viability coincided with peak values of RT activity.

Total cellular RNA was prepared from HIV-infected RL-5 cultures taken at days 7, 11 and 18 post-infection. Mock and infected cell RNA preparations were then examined by Northern blot hybridization using as probe a 6.5 kb cloned HIV DNA fragment, pBENN 5, that includes the entire HIV proviral genome lacking the 3' open reading frame (B gene) and long terminal repeats. Viral transcripts can be detected as early as 7 days post-infection, before RT activity is detectable above background. Five reactive RNA species were seen on day 11 where RT activity begins to approach peak levels. These included the full-length 9.1 kb viral genomic RNA and four subgenomic RNA species of 5.5, 5.0, 4.3 and 1.8 Kb. Viral messages were barely detectable by day 18 post infection at which point RT activity was well below peak values.

In order to determine whether HIV proteins were translated and processed in infected rabbit cultures, cell lysates were subjected to Western blot analyses. Lysates were prepared from infected RL-5 and 6083 cultures at various times after infection; RT activity reached peak values in this experiment about day 9 (6083 cultures are RT negative). Lysates derived from RL-5 or from 6083 infected with HIV were positive for viral proteins when immunoblotted with AIDS patient serum and similar proteins were not present in lysates from mock-infected cells. A positive control lysate (A3.01) contained all immunoreactive proteins identified by the serum utilized. The data represent two different exposure times of the developed Western blot. A culture of A3.01 infected at the same time as the rabbit cells was sampled on the same days as 6083 and RL-5. There is perfect correspondence between the sizes of bands detected in the human and rabbit cell lysates although the human cell appears to produce higher levels of viral proteins. Bands corresponding to p18, p24, gp41, p55, p64 and gp120 are readily detectable in HIV infected rabbit cell lysates indicating that synthesis and processing of viral proteins occurs in the rabbit cell lines.

The evidence presented herein supra, clearly indicates that, unlike cells from other nonprimate experimental animal systems, at least two rabbit T-cell lines and one macrophage cell line are susceptible to HIV infection in vitro. With the exception of the macrophage cell line, 6083, attempts to infect continuous rabbit cell lines of nonlymphoid origin as well as primary lymphoid cultures were not successful. Verification that the cell lines utilized (RL-5, 446, and 6083) are of rabbit origin was given by reactivity with rabbit specific antibodies. RL-5 has been extensively characterized with respect to the presence and expression of immunoglobulin, major histocompatibility and T-cell receptor genes. The macrophage line 6083 has likewise been extensively investigated with regard to derivation and lineage. The possibility of contamination with human cells was eliminated by the failure of DNA from normal and infected RL-5, 446 and 6083 cells to hybridize with a probe for the human Alu repeat sequence (data not shown).

It is noteworthy that the majority of cellular prerequisites necessary for productive infection are similar for rabbit and human cells. For example, HIV has been shown to be predominantly T-cell or macrophage/monocyte tropic for replication in the human and the data presented herein indicate the same to be true in the rabbit. In addition, the transforming viruses for the RL-5, 446 and 6083 cell lines, *Herpesvirus ateles*, HTLV-1 and SV40, respectively, belong to viral families which have been shown to upregulate HIV production in human systems. Events that occur following HIV infection of rabbit T-cell cultures such as appearance of RT activity, viral RNA production, a drop in cell viability and positive immunofluorescence are similar to those seen in human infections (Folks, et al, 1985, *Proc. Natl. Acad. Sci. U.S.A.* 82, 4539–4543).

TABLE 4

Infection of rabbit Cells with HIV-1

| Culture | Description | RT activity[a] | Passage[b] |
|---------|-------------|----------------|------------|
| RL-5 | Continuous T-cell line | + | + |
| 446 | Continuous T-cell line | + | + |
| 6083 | Continuous macrophage line | − | + |
| PBL | Peripheral Blood Lymphocytes | − | − |
| ConA PBL | Con-A PBL | − | − |
| PHA PBL | PHA PBL | − | − |
| IL-2 PBL | IL-2 supplemented PBL | − | − |
| PBL-MLR | PBL mixed lymphocyte reaction | − | − |
| 5943 | Breast adenocarcinoma | − | − |
| 6057 | Breast adenocarcinoma | − | − |
| Yc/c LIV | Liver fibroblast | − | − |
| UtFib | Uterine fibroma | − | − |
| R-2 | Rabbit fibroblast | − | − |

[a]Reverse transcriptase determined as described in cell-free supernatants of cultures 7 to 60 day post infection.
[b]Ability of cell-free supernatants to induce syncitia formation and RT activity in cultures of SupT1 a human T-cell line.

Utility of the rabbit model

The availability of a system for infection of rabbits with HIV-1 can now serve as an experimental tool for the study of acquired immunodeficiency syndrome (AIDS) and can be employed for such purposes as listed below.

(1) The development of vaccines and other immunization procedures designed to prevent infection with HIV-1 and/or to prevent subsequent development of AIDS in infected (seropositive) humans (e.g., procedures designed to maximize neutralizing antibody production).

(2) Development and testing of prophylactic and therapeutic drugs and procedures including passive immunization with antibodies to prevent and combat AIDS in humans.

(3) Determination of the modes by which the virus may be spread from one individual to another and to identify risk factors leading to infection with the AIDS virus.

(4) Studies that aim to determine the natural course of the immunodeficiency disease that follows HIV-1 infection and to identify cells and organs that can harbor HIV-1; to determine conditions that cause onset of overt disease in infected individuals and to develop preventive measures against this onset.

(5) Testing various isolates of HIV-1 in order to determine whether there are significant differences in the ability of different strains of HIV-1 to cause disease; the mutants may be of natural origin or may be prepared in the laboratory using recombinant DNA techniques.

(6) To test whether there are HIV-1 variants that have specific organ tropism which preferentially cause specific disease symptoms; for example neurologic rather than immunologic disorders.

(7) To determine if there are synergistic effects caused by infection with two retroviruses, for example HIV-1 introduced in conjunction with or subsequent to infection with HTLV-1.

(8) To determine whether there are synergistic effects caused by infection with HIV-1 along with other agents such as the syphilis organism or helper viruses that have been implicated in increased risk to AIDS.

(9) To determine whether there are synergistic effects in HIV-1 infection caused by use of certain drugs or other substances.

(10) To determine whether different cellular mechanisms of HIV-1 infection are equally efficient, for example if HIV-1 infected T-cells are more or less efficient at causing infection than are infected macrophages, whole blood samples, bone marrow or ejaculates and to learn which routes of infection are most efficient.

(11) To determine if genetic factors including major histocompatibility complex genes, T-cell receptor genes, immunoglobulin allotype genes, red blood cell antigens or other heritable factors play a role in resistance or predisposition to infection with HIV-1 or to the type or severity of disease that follows upon infection with HIV-1.

(12) To ascertain the in vivo contribution of cell surface molecules such as human CD4 to susceptibility to HIV-1 infection.

(13) To assess factors involved in passage of HIV-1 from mother to offspring and to measure susceptibility as related to age of animals.

It is noted that given the model system of the present invention, all of the above-mentioned utilities can be routinely accomplished without specific elaboration herein of the procedures involved, it being pointed out that such procedures are quite standard and well known to one of ordinary skill in the art to which this invention belongs. Thus, a method for testing anti-AIDS therapeutic agent, comprises (a) administering a therapeutic agent to be tested, to live HIV-infected rabbit; and (b) determining the effect of said agent on the progression of HIV-1 infection in said rabbit, an arresting of the progression of HIV-1 infection in said rabbit being indicative of the efficacy of said agent.

Similarly, a method for testing anti-AIDS vaccine comprises (a) administering an anti-AIDS vaccine to be tested, to a group of live uninfected rabbits; and (b) the infecting the rabbits of step (a) with human T-cells infected in vitro with HIV-1 while concomitantly infecting a second control group of uninfected rabbits with the same batch of human T-cells infected in vitro with HIV-1, a failure of HIV-1 infection developing in the rabbits of group (a) and the progression of HIV-1 infection in control group of rabbits being indicative of the efficacy of the anti-AIDS vaccine.

Use of rabbit model for diagnosis of AIDS infection in human subjects

The present invention can also be used for in vivo diagnostic tests for infection with HIV-1 in human subjects. The standard method for determining whether an individual is infected with HIV-1 and therefore at high risk for the disease AIDS is to determine if that individual has antibodies directed against any or all of the proteins that comprise the HIV-1 virion. This is accomplished by the use of immunologic assays such as the ELISA or the immunoblot (Western blot) procedures. There are circumstances (such as babies born of seropositive mothers or individuals given vaccines against HIV-1) in which the antibody test does not suffice to determine the infection status of an individual. When it is not possible to use these means to determine infection status, other more complicated and less efficient means must be applied to test samples from the subject. Certain tests require a relatively large amount of blood for cell isolation and culture of virus and a negative result is not a certain indicator that the subject is free of infection.

It has been demonstrated herein that rabbits are susceptible to infection with HIV-1 and that infection in these animals can be monitored by changes in seroreactivity using simple serologic tests similar to those used for human samples. This finding can be used as the basis for a diagnostic test for HIV-1 infection in human subjects. The test can be applied in those cases where determination of seropositivity does not render a satisfactory answer, such as for testing babies born of mothers infected with HIV-1 and therefore seropositive for HIV-1 proteins because maternal antibody persists in the circulation for a considerable period after birth. Clearly, there is a need to identify babies that are infected with the virus by tests that do not involve the determination of antibody. This is necessary so that treatment may begin as soon as possible in infected babies and so that those that are merely seropositive, but not infected, can be spared the potentially deleterious side effects of the treatment regimens. In addition, this test may be useful in determining the infection status in individuals immunized with HIV-1 vaccines.

The test in accordance with the present invention comprises intravenous injection of rabbits with whole blood samples from individuals suspected to be infected with HIV-1; serologic testing of the rabbits is then carried out to determine whether the sample is infectious. More detailed testing of the rabbits for infection would involve culture of lymphocytes and tests for HIV-1 proteins in the culture. As an alternative, the white cell complement (WBC) of the human blood sample is isolated and used for injection of the rabbits. The infectivity of the samples could be enhanced by culture in the presence of stimulators such as PHA and IL-2, well known to one of ordinary skill in the art. Procedures for selection and injection of the rabbits and other tests are the same as described herein, supra.

It is understood that the examples and embodiments described herein are for illustrative purposes only and that various modifications in light thereof will be suggested to persons skilled in the art and are to be included within the spirit and purview of this application and scope of the appended claims.

What is claimed is:

1. A method for testing an anti-HIV-1 therapeutic agent, comprising:
    (a) infecting a live rabbit with HIV-1 by administering to the rabbit human T-cells infected with HIV-1;
    (b) administering a therapeutic agent to be tested to the HIV-1 infected rabbit; and
    (c) determining the effect of said agent on the progression of HIV-1 infection in said rabbit, an arresting of the progression of HIV-1 infection in said rabbit being indicative of the efficacy of said agent.

2. A method for testing an anti-HIV-1 vaccine, comprising
    (a) administering an anti-HIV-1 vaccine to be tested to a group of live uninfected rabbits; and
    (b) infecting the rabbits of step (a) with HIV-1-infected human T-cells while concomitantly infecting a second control group of uninfected rabbits with the same batch of HIV-1 infected human T-cells, a failure of HIV-1 infection developing in the rabbits of group (a) and the progression of HIV-1 infection in control group of rabbits being indicative of the efficacy of the anti-HIV-1 vaccine.

3. The method of claim 1, wherein in step (a) the human T-cells are infected with HIV-1 in vitro.

4. The method of claim 1, wherein in step (c) the effect of said agent on the progression of HIV-1 infection is determined by assaying for HIV-1 specific antibodies, antigen, genomic viral sequences or RNA transcripts in said rabbit.

5. The method of claim 1, wherein said rabbit contains a foreign gene encoding a molecule to enhance infection with HIV-1.

6. The method of claim 4, wherein the rabbit is co-infected with HTLV-I.

* * * * *